United States Patent [19]

Le

[11] Patent Number: 4,735,802

[45] Date of Patent: Apr. 5, 1988

[54] TOPICAL DERMATOLOGICAL COMPOSITION AND METHOD OF TREATMENT

[76] Inventor: Bich N. Le, 112 Old Oak Ct., Pontiac, Mich. 48055

[21] Appl. No.: 859,426

[22] Filed: May 5, 1986

[51] Int. Cl.$^4$ ............................................. A61K 33/06
[52] U.S. Cl. ..................................... 424/154; 514/859
[58] Field of Search .................. 424/154; 514/949, 859

[56] References Cited

U.S. PATENT DOCUMENTS 4,640,932  2/1987  Fona et al. .......................... 514/714

OTHER PUBLICATIONS

Kirk–Othmer, Encyclopedia of Chemical Technology, 2nd Ed., vol. 4, pp. 14–27 (1966).

Primary Examiner—Leonard Schenkman
Attorney, Agent, or Firm—Krass & Young

[57] ABSTRACT

A topical dermatological composition and method are provided for treating dermatoses that are characterized by lesion sites, exudate, and chronic inflammation of the sebaceous glands and follicles of the skin. One preferred form is a sterile homogeneous settable therapeutic paste composition comprising a mixture of water and dired calcium sulfate.

9 Claims, No Drawings

TOPICAL DERMATOLOGICAL COMPOSITION AND METHOD OF TREATMENT

TECHNICAL FIELD

This invention concerns a dermatological composition or dosage form, and method of topical treatment using the composition for therapy and remission of dermatoses and other disorders of the pilosebaceous glands characterized by skin lesion sites, exudate and inflammation.

Certain dermatoses, such as for example acne, involve disorders in the oil glands associated with hair follicles, the so called "pilosebaceous apparatus." These diseases are characterized by inflammation of the hair follicles and/or sebaceous glands and in some instances are marked by disfiguring papules, pustules, nodules or crusts. These diseases are frequently chronic and in many individuals are highly resistant to cure.

Many medicinals have been used in the treatment of such disorders of the pilosebaceous apparatus. Among the most effective remedial agents are resorcinol and resorcinol monoacetate which function by virtue of their keratolytic and/or keratoplastic effect, the particular effect depending principally on the concentration of the active ingredient. Dermatological preparations including resorcinol, resorcinol monoacetate or other phenolic compounds are frequently supplied as ointments in oleaginous bases, usually petrolatum with or without fats and waxes and may or may not include anodynes, such as for example bismuth subnitrate, zinc oxide, talc, etc. The effectiveness of resorcinol or other hydroxy aromatic compounds in treatment of disorders of the pilosebaceous system is reduced by the presence of oleaginous material therewith since such oleaginous material interferes with the activity of the therapeutic component of the composition. Accordingly, resorcinol is frequently employed in the form of a dilute solution or lotion when used to treat certain dermatoses. However, the use of flowable preparations for the purpose is highly undesirable particularly when the face is the site of the disorder treated because drippings of the medicament from said site can be unpleasant if not noxious, particularly to the hair, eyes, mouth or clothing of the patient. Hence, hydroxy aromatic therapeutic agents are advantageously applied in thickened systems. Ideally the therapeutic agent is incorporated in a hydrophilic base whereby the composition resists flow unless sufficient mechanical force is applied thereto. An advantage inherent in the use of a gel is that the total quantity of treating material topically applied to any cutaneous site is susceptible to control. Resorcinol preparations including a variety of hydrophilic colloids as the vehicle have been used in medicinals. However, the efficacy of resorcinol in such preparations as have been heretofore available is essentially that of the resorcinol in the absence of said colloid. An improved system that is thickened and has enhanced efficacy is the system employing resorcinol and colloidal attapulgite, as described in U.S. Pat. No. 3,137,622. A continuing problem with these medicinals, however, is that the hydroxy aromatic compounds can be irritating to the skill and mucous membranes. The compounds also can be toxic when absorbed systemically. A similar system which can present a problem with irritation, is described in U.S. Pat. No. 4,388,301 employing a caustic compound, viz. a metal polysulfide compound in a powder carrier comprising montmorillonite and attapulgite.

It is therefore an object of the present invention to provide means for treating dermatoses such as those characterized by acne lesions, exudate and inflammation, while avoiding or minimizing the use of medicinals such as caustic metal compounds and phenolic aromatic compounds that are potentially irritating to the skin.

It is also an object of the invention to provide means as described which in use are essentially harmless to the hair, eyes, skin and clothing.

These and other objects, features and advantages of the invention will be seen from the following description.

SUMMARY AND DETAILED DESCRIPTION OF THE INVENTION

The invention in one aspect concerns a method of treating dermatoses or skin diseases that are characterized by lesion sites, exudate, and chronic inflammation of the sebaceous glands and follicles of the skin. The method includes the steps of providing a sterile, homogeneous, settable therapeutic paste composition comprising a mixture of water and dried calcium sulfate, which mixture optionally may contain other ingredients or components that are compatible in the proportion employed, applying the paste to the skin area comprising the lesion sites in a co-extensive overlying soft mask or layer, allowing the mask to set until hard and to remain in place on the skin for a time sufficient to become dry and achieve absorption and adsorption of exudate, optionally removing the thus sorbed exudate by aseptic removal of the mask from the skin and, if necessary, repeating the regimen of treatment steps periodically until remission of the lesions is achieved. The therapeutic paste composition employed, described in greater detail hereinafter, is selected to have a uniform consistency that on the one hand has sufficient body and moisture to enable applying and working the composition in a co-extensive uniformly thick layer over the skin area being treated and on the other hand is not so moist that the material is unmanageably liquid and thus apt to erode and drip or run off from the treatment area and tend to leave there a covering layer of uneven non-uniform thickness. The paste composition, as indicated, is applied to the skin area comprising the lesion sites which sites may typically include one or more of the facial, scapular, presternal and shoulder areas. The paste composition is applied at ambient temperature. Once applied and if necessary formed by shaping while workable to a suitable uniform thickness (e.g. about ⅛ to about ¼ inch), the mask is allowed to set until hard. In its hard set condition, the mask is a structurally rigid monolithic plate-like layer that has substantial compressive and tensile strength. The mask closely conforms to the surface of the skin and its lesions and pores. Occlusive bandaging is not required. The mask importantly tends to invade and fill up the pores and lesions, providing benefit especially in the pores and lesions that are chronically inflamed. One aspect of benefit is that the mask affords an adverse environment for the microbial skin flora. Another aspect is that, as indicated, the mask serves to sorb skin oil and sebaceous exudate. Further, the mask is hygroscopic so that as applied and allowed to set and become dry, it withdraws moisture from and dries the skin, thereby creating a cooling sensation and having an astringent or shrinking effect upon the skin. For best results, the mask is kept in place undisturbed until completely dry. Optionally, it can be removed aseptically by suitable means such as washing and drying the skin. Conveniently the mask can be applied and set before bedtime in the evening and during the night, allowed to fall off or slough off as when completely dry. The second application of the mask typically can be undertaken in a short period, e.g. with the next few hours. To a considerable extent, the effectiveness of the therapy depends on the number of successive applications. Typically, a beneficial result can be observed within several days, usually within about 3 to 5 days, in a regimen where the treatment is given each day or preferably each night, as described. The papules first lose their edematous, erythematous appearance, they then shrink and finally disappear. For difficult, deepseated inflammatory lesions, the progressive healing starts as the reduction of firmness, then shrinkage of lesions, and the eventual disappearance of the lesions, with absence of or minimal scarring.

In another aspect, the invention concerns a dermatological composition adapted for topical treatment of dermatoses of the kind described, comprising a sterile homogeneous therapeutic paste made by mixing a water component and dried calcium sulfate in fine powder form that essentially is an odorless, tasteless hemihydrate. In one preferred embodiment, the composition is packaged with the water component and the dried powder component in separate sealed containers. The paste is of a non-flowing consistency that can be worked or formed into a layer covering a selected area of the skin and being settable to a hard mass on standing. The water component in one preferred embodiment optionally contains a water soluble thickener such as sodium carboxymethyl cellulose in an amount sufficient to cause the water component to gel and prevent the water component from flowing. The water component suitably may contain a self sterilizing agent which may be conventional and preferably is trichlocarban, oxychlorosene sodium or triclosan constituted in dilute solution e.g. 0.1–0.2%. Suitable topical anti-infectives are described in The Nurses Guide to Drug Therapy, Chapter 88, Prentice-Hall, Inc., 1984.

The paste in one preferred embodiment includes a per se effective amount of a compatible anodyne such as zinc oxide. As constituted if necessary with buffering, the paste is essentially at neutral pH.

A preferred compositon for treating dermatoses is a smooth workable paste made by mixing sterile water with heat-sterilized calcium sulfate hemihydrate, in the weight ratio of 4 parts to about one part; optionally with thickener, buffer, anti-infective agent and/or anodyne.

Having thus described my invention, the embodiments in which an exclusive property or privilege is claimed are defined as follows:

1. A method of treating dermatoses that are characterized by lesion sites, exudate, and chronic inflammation of the sebaceous glands and follicles of the skin, including the steps of:

(a) applying a sterile homogeneous settable therapeutic paste composition consisting essentially of a mixture of water and dried calcium sulfate, to the skin area comprising the lesion sites in a co-extensive overlying soft mask or layer, (b) allowing the mask to set until hard and to remain in place on the skin for a time sufficient to become dry and achieve absorption and adsorption of exudate, (c) allowing the mask to slough off or optionally removing the thus sorbed exudate by aseptic removal of the mask from the skin;

and, if necessary repeating the regimen of steps a, b and c periodically until remission of the lesions is achieved.

2. The method of treating acne according to claim 1 where the regimen of steps a, b and c is carried out once daily for several days until remission of the lesions is achieved.

3. The method of treating acne according to claim 1 where the regimen of steps a, b and c is carried out once each night for several nights until remission of the lesions is achieved.

4. A dermatological composition adapted for topical treatment of dermatoses that are characterized by lesion sites, exudate and chronic inflammation of the sebaceous glands and follicles of the skin, consisting essentially of a sterile homogeneous therapeutic paste made by mixing a water component containing a self-sterilizing agent in an amount sufficient to maintain sterility of the composition, and dried calcium sulfate in fine powder form that essentially is an odorless tasteless hemihydrate, the paste being of a non-flowing consistency that can be worked or formed into a layer covering a selected area of the skin and being settable to a hard mass on standing.

5. A composition according to claim 4 where the self-sterilizing agent is selected from trichlorcarban, oxychlorosene sodium and triclosan.

6. A composition according to claim 4 where the paste includes a per se effective amount of a compatible anodyne agent.

7. A composition according to claim 4 where the paste is essentially at neutral pH.

8. A dermatological composition adapted for topical treatment of dermatoses that are characterized by lesion sites, exudate and chronic inflammation of the sebaceous glands and follicles of the skin, consisting essentially of a sterile homogeneous therapeutic paste made by mixing a water component and dried calcium sulfate in fine powder form that essentially is an odorless tasteless hemihydrate, the paste being of a non-flowing consistency that can be worked or formed into a layer covering a selected area of the skin and being settable to a hard mass on standing, the water component containing water soluble carboxymethyl cellulose in an amount sufficient to cause the water component to gel and prevent the water component from flowing.

9. A composition according to claim 8 where the paste includes a self-sterilizing agent.

* * * * *